(12) United States Patent
Nioutsikou

(10) Patent No.: US 10,729,919 B2
(45) Date of Patent: Aug. 4, 2020

(54) METHOD FOR SUPPORTING RADIATION TREATMENT PLANNING FOR A PATIENT

(71) Applicant: Siemens Healthcare GmbH, Erlangen (DE)

(72) Inventor: Elena Nioutsikou, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 267 days.

(21) Appl. No.: 15/710,931

(22) Filed: Sep. 21, 2017

(65) Prior Publication Data

US 2018/0099152 A1    Apr. 12, 2018

(30) Foreign Application Priority Data

Oct. 7, 2016 (DE) .................. 10 2016 219 496

(51) Int. Cl.
*A61N 5/10* (2006.01)
*G06T 7/12* (2017.01)
*G06T 7/00* (2017.01)

(52) U.S. Cl.
CPC ......... *A61N 5/1039* (2013.01); *A61N 5/1038* (2013.01); *A61N 5/1049* (2013.01); *G06T 7/0014* (2013.01); *G06T 7/12* (2017.01); *A61N 2005/1055* (2013.01); *A61N 2005/1061* (2013.01); *G06T 2207/10088* (2013.01); *G06T 2207/20084* (2013.01); *G06T 2207/20128* (2013.01); *G06T 2207/30096* (2013.01)

(58) Field of Classification Search
CPC ..... A61N 5/1039; A61N 5/1049; A61N 5/103
USPC ....................................... 600/1–8
See application file for complete search history.

(56) References Cited

U.S. PATENT DOCUMENTS

2007/0263769 A1    11/2007   Roell
2011/0007959 A1    1/2011   Schulz et al.
(Continued)

FOREIGN PATENT DOCUMENTS

CN     1595451 A    3/2005
CN    101959454 A    1/2011
(Continued)

OTHER PUBLICATIONS

A. Torrado-Carvajal et al: "Fasl pseudo-CT synthesis MRI TI-weighted images using a patch-based approach", Proceedings Optical Diagnostics of Living Cells II, XP055448905, pp. 968103, vol. 9681; 2015.

(Continued)

Primary Examiner — John P Lacyk
(74) Attorney, Agent, or Firm — Harness, Dickey & Pierce, P.L.C.

(57) ABSTRACT

A method is disclosed for supporting radiation treatment planning for a patient. In an embodiment, the method includes acquiring computed tomography image data for the patient, which has been acquired from the patient using a computed tomography device; allocating magnetic resonance image data to the computed tomography image data using the computed tomography image data, wherein the magnetic resonance image data has been acquired from at least one examination subject that differs from the patient using a magnetic resonance unit; and providing the computed tomography image data together with the magnetic resonance image data allocated to the computed tomography image data to support the radiation treatment planning for the patient.

25 Claims, 3 Drawing Sheets

(56) References Cited

U.S. PATENT DOCUMENTS

| | | |
|---|---|---|
| 2012/0082354 A1 | 4/2012 | Peters et al. |
| 2014/0307936 A1 | 10/2014 | Dore et al. |
| 2015/0367145 A1 | 12/2015 | Sjölund et al. |
| 2016/0086330 A1 | 1/2016 | Bjoern |

FOREIGN PATENT DOCUMENTS

| | | |
|---|---|---|
| CN | 102460509 A | 5/2012 |
| CN | 104093354 A | 10/2014 |
| DE | 102006021771 A1 | 11/2007 |
| DE | 102014218924 A1 | 3/2016 |
| WO | WO-2009/109874 A1 | 9/2009 |
| WO | WO-2010/150156 A1 | 12/2010 |
| WO | WO-2013/086580 A1 | 6/2013 |
| WO | WO 2015171056 A1 | 11/2015 |

OTHER PUBLICATIONS

Onjukka, E. et al; "Does Prostate Radiation Therapy Treatment Planning Benefit From MRI?"; in Lax International Journal of Radiation Oncology; vol. 93; No. 3S; Poster Viewing Session E569; Supplement 2015.

Jonsson, Joakim H. et al: "Treatment planning of intracranial targets on MRI derived substitute CT data"; in Radiotherapy and Oncology; No. 108; pp. 118-122; (2013).

Dowling, Jason A.; "An Atlas-Based Electron Density Mapping Method for Magnetic Resonance Imaging (MRI)-Alone Treatment Planning and Adaptive MRI-Based Prostate Radiation Therapy"; in: International Journal of Radiation Oncology, 2012, vol. 83, No. 1, pp. 5-11.

Torrado-Carvajal, Angel et al; "Fast Patch-Based Pseudo-CT Synthesis from Tl-Weighted MR Images for PET/MR Attenuation Correction in Brain Studies"; in The Journal of Nuclear Medicine; vol. 57; No. 1; pp. 136-143, Jan. 2016.

Albrecht, Moritz H. et al; "Assessment of an Advanced Monoenergetic Reconstruction Technique in Dual-Energy Computed Tomography of Head and Neck Cancer"; in Eur Radiol; European Society of Radiology 2015; DOI 10.1007/s00330-015-3627-1.

Hsu, Shu-Hui et al; "Investigation of a method for generating synthetic CT models from MRI scans of the head and neck for radiation therapy"; in: Phys Med Biol.; vol. 58; No. 23; Dec. 7 2013; DOI:10.1088/0031-9155/68/23/8419.

Greer, Peter B. et al; "A magnetic resonance imaging-based workflow for planning radiation therapy for prostate cancer"; in MJA; vol. 194; No. 4; pp. S24-S27; Feb. 21, 2011.

First Office Action dated Sep. 4, 2019 in Chinese Application No. 201710913801.0.

Second Office Action dated Apr. 8, 2020 in Chinese Application No. 201710913801.0.

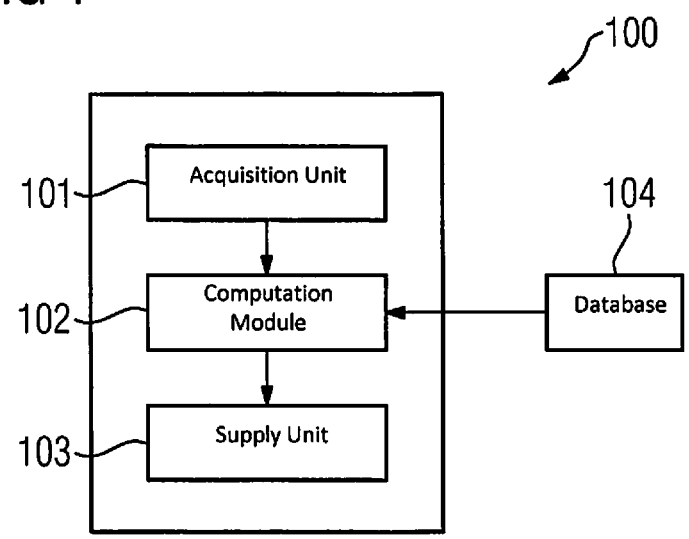
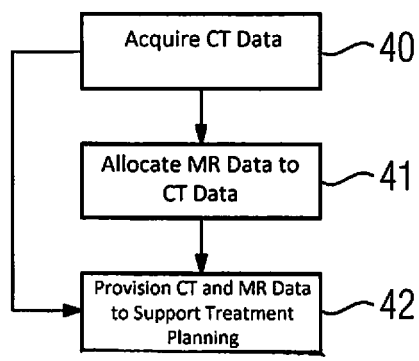

METHOD FOR SUPPORTING RADIATION TREATMENT PLANNING FOR A PATIENT

PRIORITY STATEMENT

The present application hereby claims priority under 35 U.S.C. § 119 to German patent application number DE 102016219496.8 filed Oct. 7, 2016, the entire contents of which are hereby incorporated herein by reference.

FIELD

At least one embodiment of the invention generally relates to a method for supporting radiation treatment planning for a patient, to a computation unit and/or to a computer program product.

BACKGROUND

In radiation therapy, a target volume, a tumor, for example, in a patient is irradiated with ionizing radiation. Here, external radiation therapy, which includes irradiation of a patient's body from outside the body, is known. Internal radiation therapy, also referred to as brachytherapy, is also known. In brachytherapy, radiation sources that include radioactive substances are placed inside a patient's body in order to damage or destroy the tumor tissue locally in the patient's body in the target volume.

Basically, when irradiating the patient, it is a challenge to ensure that an adequate dose of radiation is applied to a target volume such that the tumor tissue contained in the target volume is destroyed. At the same time, organs at risk surrounding the target volume need to be spared as much as possible. Hence a high level of accuracy is very important in the planning of the radiation treatment.

Planning and/or monitoring radiation therapy or radiation treatment of a patient by way of imaging is/are known. A radiation treatment plan is usually drawn up for this purpose with the aid of medical imaging data from the patient that has been generated using a three-dimensional imaging method. Computed tomography image data (CT image data) is generally used for this. From the computed tomography image data, on the one hand the target volume for radiation therapy can be established, and on the other hand, surrounding organs at risk can be located.

Furthermore, the intensity values for the image voxels in the image data (measured in "Hounsfield Units") depict a close approximation of an electron density at the corresponding location in the patient's body because the intensity values for the image voxels are based on an absorption of X-rays at the relevant locations. In this way, the computed tomography image data for planning the radiation treatment can be converted into an electron density map in a really simple way.

In a radiation treatment, because the intensity of the interaction of the radiation is correlated with the electron density in the body, the attenuation of the radiation as it goes through the body can be calculated in a comparatively simple manner from the computed tomography image data. Due to this property, computed tomography image data has hitherto been used preferentially when drawing up a radiation treatment plan. Furthermore, computed tomography image data has only a slight geometrical distortion and consequently allows an appropriate definition of a reference geometry for the planning of the radiation treatment and carrying out the radiation treatment.

Nevertheless, there is a demand for other imaging methods that have a better soft tissue contrast to be used when planning the radiation treatment in order to allow an improved identification of the tumor tissue in the target volume and/or of the organs at risk. Such an imaging method that meets the demand for a better soft tissue contrast is magnetic resonance imaging (MR imaging) using a magnetic resonance unit. In such imaging, the contrast is dependent on the distribution of the spin density, the interaction of the spins with one another and/or with their surroundings. In this way, a soft tissue contrast can be achieved that is clearly superior to the contrast achievable with a computer tomography system.

In a magnetic resonance unit, also known as a magnetic resonance tomography system, the body that is to be examined of an examination subject, in particular of a patient, is exposed with the aid of a main magnet to a relatively high main magnetic field, of for example 1.5 or 3 or 7 Tesla. In addition, gradient pulses are applied with the aid of a gradient coil unit. High frequency pulses, in particular excitation pulses, are then emitted via a high frequency antenna unit using appropriate antenna devices, which leads to the nuclear spins of certain atoms, resonantly excited by these high frequency pulses, being flipped round a defined flip angle against the magnetic field lines of the main magnetic field. When the nuclear spins are relaxed, high frequency signals known as magnetic resonance signals are emitted, which are then received by appropriate high frequency antennas and then further processed. The desired image data can then finally be reconstructed from the raw data acquired in this way.

Such a combined use of computer tomography imaging and magnetic resonance imaging is known for planning a radiation treatment. For the planning of the radiation treatment, the acquired computed tomography image data and magnetic resonance image data are then typically superimposed by way of image registration. In so doing, however, the problem may occur that an image registration that is not carried out completely correctly can introduce systematic errors into the planning of the radiation treatment. In addition, with the combined use of computer tomography imaging and magnetic resonance imaging, the image data has to be acquired with the two modalities spaced a short distance away from each other so that changes in the patient's anatomy, due for example, to differences in how full the patient's bladder is, can be avoided from one data acquisition to another. This can lead to operational challenges, increased costs, and reduced patient comfort as the patient has to suffer a number of examinations.

SUMMARY

At least one embodiment of the invention allows for improved support for the radiation treatment planning for the patient. Advantageous embodiments are described in the claims.

The method, according to at least one embodiment of the invention, for supporting radiation treatment planning for a patient includes the following:

acquiring computed tomography image data relating to the patient, which has been acquired from the patient via a computed tomography device;

allocating magnetic resonance image data to the computed tomography image data using the computed tomography image data, the magnetic resonance image data having been acquired from at least one examination subject that differs from the patient via a magnetic resonance unit; and providing the computed tomography image data together with the magnetic resonance image data allocated to the computed tomography image data to support the radiation treatment planning for the patient.

At least one embodiment makes provision for the allocation of the magnetic resonance image data to the computed tomography image data to be achieved using an atlas-based method, the method comprising:

provision of an atlas, which includes the magnetic resonance image data together with corresponding atlas-based computed tomography image data for the at least one examination subject that differs from the patient, allocation of the atlas-based computed tomography image data to the computed tomography image data, allocation of the magnetic resonance image data to the computed tomography image data using information, which is derived from the allocation of the atlas-based computed tomography image data to the computed tomography image data.

A further method according to at least one embodiment of the invention to support radiation treatment planning for the patient includes the following:

acquiring computed tomography image data from the patient, which has been acquired from the patient using a computed tomography device;

providing an artificial neural network that has been trained to segment an organ structure based on corresponding training magnetic resonance image data and training computed tomography image data;

segmenting the organ structure in the computed tomography image data applying the trained artificial neural network to an image content of the computed tomography image data; and providing the computed tomography image data together with the segmented organ structure to support the radiation treatment planning for the patient.

The computation unit, according to at least one embodiment of the invention, includes at least one computation module, the computation unit being designed to perform a method according to at least one embodiment of the invention.

Therefore, the computation unit in particular is designed to carry out computer-readable instructions in order to perform the method according to at least one embodiment of the invention. In particular, the computation unit includes a memory unit, computer-readable memory data being stored in the memory unit, the computation unit being designed to load the computer-readable data from the memory unit and to run the computer-readable data in order to carry out a method according to at least one embodiment of the invention.

The computer program product according to at least one embodiment of the invention can be loaded directly into a memory of a programmable computation unit and comprises program-coding segments in order to perform a method according to at least one embodiment of the invention when the computer program product is run in the computation unit. The computer program product can be a computer program or include a computer program. As a result thereof, the method according to at least one embodiment of the invention can be carried out quickly, in an identically repeatable manner, and robustly.

The computer program product of at least one embodiment is stored on a computer-readable medium, for example, or on a network or server from which it can be loaded into the processor of a local computation unit that can be directly connected thereto or designed as a component thereof.

Furthermore, control data relating to the computer program product can be stored on an electronically readable data carrier. The control data on the electronically readable data carrier can be designed such that it carries out a method according to the invention when the data carrier is used in a computation unit. The computer program product can therefore also be the electronically readable data carrier. Examples of electronically readable data carriers are a DVD, a magnetic tape, a hard disk, or a USB stick, on which electronically readable control information, in particular software (see above), is stored. When this control information (software) is read by the data carrier and stored in a control device and/or computation unit, all the inventive embodiments of the method described in the aforementioned can be carried out. The invention can therefore also take as its point of departure the computer-readable medium and/or the electronically readable data carrier.

BRIEF DESCRIPTION OF THE DRAWINGS

The invention is described and explained below in greater detail using the embodiments set out in the figures.

The drawings show:

FIG. 1 a computation unit according to an embodiment of the invention to carry out a method for supporting radiation treatment planning for a patient, FIG. 2 a first embodiment of a method for supporting radiation treatment planning for a patient, FIG. 3 a second embodiment of a method for supporting radiation treatment planning for a patient, FIG. 4 an embodiment of a further method for supporting radiation treatment planning for a patient, which uses an artificial neural network, and FIG. 5 a computed tomography device for acquiring computed tomography image data from the patient.

DETAILED DESCRIPTION OF THE EXAMPLE EMBODIMENTS

Figure 3:
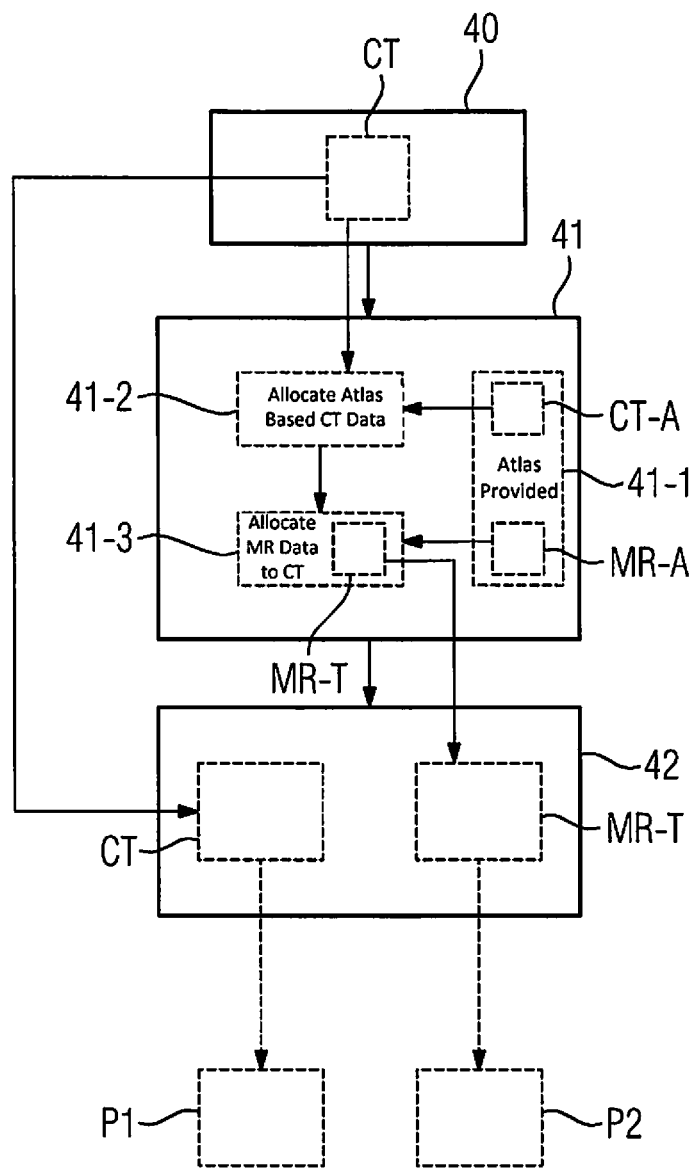

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method, according to at least one embodiment of the invention, for supporting radiation treatment planning for a patient includes the following:

acquiring computed tomography image data relating to the patient, which has been acquired from the patient via a computed tomography device;

allocating magnetic resonance image data to the computed tomography image data using the computed tomography image data, the magnetic resonance image data having been acquired from at least one examination subject that differs from the patient via a magnetic resonance unit; and providing the computed tomography image data together with the magnetic resonance image data allocated to the computed tomography image data to support the radiation treatment planning for the patient.

The acquisition of the computed tomography image data can directly include the acquisition of the computed tomography image data using the computed tomography device. Alternatively, the acquisition of the computed tomography image data can include loading computed tomography image data already acquired from the patient from a database. In all cases, the computed tomography image data included in particular anatomical image information for the particular patient who is to be irradiated.

The allocation of the magnetic resonance image data to the computed tomography image data can ensue by way of an algorithm, which has the magnetic resonance image data and the computed tomography image data as input parameters and the magnetic resonance image data allocated to the computed tomography image data as output parameters. The algorithm inputs the computed tomography image data itself so that the allocation of the magnetic resonance image data to the computed tomography image data is possible, a direct registration of the magnetic resonance image data onto the computed tomography image data being conceivable. Since this is often technically difficult to achieve, however, an atlas-based method is used for allocating the magnetic resonance image data to the computed tomography image data. Options for the atlas-based method are described in even greater detail in one of the paragraphs that follow.

The magnetic resonance image data is loaded for allocation to the computed tomography image data from a database in particular. Advantageously, as described in further detail in one of the paragraphs that follow, the database can include an atlas that includes the magnetic resonance image data together with corresponding atlas-based computed tomography image data. In particular exclusively, the magnetic resonance image data has been acquired via a magnetic resonance unit from the at least one examination subject that differs from the patient. This means that in particular the patient does not have to be examined via the magnetic resonance unit in order to create the magnetic resonance image data.

Advantageously, the magnetic resonance image data from a plurality of examination subjects that differ from the patient has been acquired via the magnetic resonance unit. In this way, the magnetic resonance image data can include, for example, average, advantageously universal anatomical features that are based on data acquisitions from the plurality of examination subjects that differ from the patient. The magnetic resonance image data can of course also have been acquired with a plurality of different magnetic resonance units if they have been acquired from a plurality of examination subjects that differ from the patient.

The result of the allocation of the magnetic resonance image data to the computed tomography image data consists in particular of the magnetic resonance image data allocated to the computed tomography image data. This magnetic resonance image data allocated to the computed tomography image data has in particular a modified image content compared to the original magnetic resonance image data.

If, for example, the allocation of the magnetic resonance image data to the computed tomography image data includes a three-dimensional transformation of the magnetic resonance image data, then the magnetic resonance image data allocated to the computed tomography image data is in particular three-dimensionally transformed compared to the original magnetic resonance image data. The magnetic resonance image data allocated to the computed tomography image data is in particular three-dimensionally adjusted to the computed tomography image data, and therefore is advantageously as far as possible in three-dimensional alignment with the computed tomography image data. The magnetic resonance image data allocated to the computed tomography image data accordingly depicts in particular an anatomy that is as far as possible in line with the patient's anatomy, on the basis of the computed tomography image data acquired from the patient. Accordingly, the magnetic resonance image data allocated to the computed tomography image data is advantageously designed such that, when the magnetic resonance image data allocated to the computed tomography image data and the computed tomography image data are superimposed on each other, anatomical structures of the patient are located in the same places in both data sets.

The provision of the computed tomography image data together with the magnetic resonance image data allocated to the computed tomography image data can include a display of the two data sets on a display unit for a user. The two image data sets can be displayed on the display unit at the same time, for example, adjacent to each other. A merged view of the computed tomography image data and the magnetic resonance image data allocated to the computed tomography image data is also conceivable on the display unit. Alternatively or additionally, the provision thereof can include storage of the two image data sets in the database. Alternatively or additionally, the provision thereof can include transmission of the two image data sets to a further processing system, an image processing system, for example, where the further computation system is then able to further process the two image data sets.

The computed tomography image data is provided in particular together with the magnetic resonance image data allocated to the computer tomography image, such that both the image data sets can contribute to supporting the planning of the radiation treatment for the patient. Here, as described in even greater detail in one of the paragraphs that follow, to support the planning of the radiation treatment, the computed tomography image data can be provided for a different purpose than the magnetic resonance image data allocated to the computed tomography image data. A planning step can therefore be attached to the provision of the computed tomography image data together with the magnetic resonance image data allocated to the computed tomography image data, in which step at least part of the planning of the radiation treatment for the patient is carried out using the computed tomography image data provided together with the magnetic resonance image data allocated to the computed tomography image data.

The proposed procedure can therefore be considered in particular as a reversal of the known exclusively magnetic resonance-based radiation treatment planning ("MR-only RT Planning", MRORTP). This exclusively magnetic resonance-based radiation treatment planning would involve completely eliminating from the planning process computer tomography imaging for suitable clinical applications. For exclusively magnetic resonance-based radiation treatment planning, it is necessary in many cases, however, to fall back on information from computer tomography imaging because an electron density map required for the dose calculation has to be drawn up. The creation of the electron density map required for the dose calculation is more typically difficult to achieve exclusively via the acquired magnetic resonance image data. Therefore, it is possible, for example, to fall back on a known atlas-based method, in which information from computed tomography image data stored in an atlas can be accessed in order to draw up the electron density map for the exclusively magnetic resonance-based radiation treatment planning.

Here, atlas-based registration methods are known for creating the electron density map for the exclusively magnetic resonance-based radiation treatment planning, reference being made for example to the paper by Dowling et al., "An Atlas-Based Electron Density Mapping Method for Magnetic Resonance Imaging (MRI)-Alone Treatment Planning and Adaptive MRI-Based Prostate Radiation Therapy", Int J Radiation Oncol Biol Phys, 83(1), e5-e11, 2012, the entire contents of which are hereby incorporated herein by reference. Alternatively, atlas-based methods, which use a patch-based method, are known. Here, reference is made, for example, to the paper by Torrado-Carvajal et al., "Fast Patch-Based Pseudo-CT Synthesis from T1-Weighted MR Images for PET/MR Attenuation Correction in Brain Studies", J Nucl Med, 57, 136-143, 2016, the entire contents of which are hereby incorporated herein by reference, where the method described in this paper can also be applied without any problems to the calculation of the electron density instead of to PET/MR attenuation correction.

Unlike the known methods described in the two previous paragraphs, in addition, information from magnetic resonance imaging can advantageously be obtained by way of the proposed method for planning the radiation treatment for the patient without an acquisition of the magnetic resonance image data from the patient being necessary. The procedure described therefore provides in particular radiation treatment planning for the patient, for which exclusively computed tomography image data has to be acquired from the patient. However, by way of the procedure described, magnetic resonance image data can also be used advantageously to support the planning of radiation treatment, without acquisition of the magnetic resonance image data from the patient being necessary. The fact that the acquisition of magnetic resonance image data can be dispensed with for the radiation treatment planning for the patient can lead advantageously to considerable simplifications in the work flow and/or lead to cost-saving and/or to an increase in patient comfort.

The magnetic resonance image data allocated to the computed tomography image data can be seen here as pseudo-MR image data since it has not been acquired directly from the patient via the magnetic resonance unit. For the planning of the radiation treatment for the patient, the magnetic resonance image data allocated to the computed tomography image data can in a particularly advantageous manner have an increased soft tissue contrast compared with the computed tomography image data. Whilst the computed tomography image data typically only shows the limits of an organ, the magnetic resonance image data allocated to the computed tomography image data can provide more specific information in a particularly advantageous manner, for example about a precise extent of the tumor tissue in the target volume and/or about a location of the organs at risk and/or about an activity of the tumor tissue. At the same time, in the magnetic resonance image data allocated to the computed tomography image data, tumor tissue and/or organs at risk can be better distinguished from the surrounding tissue than in the computed tomography image data. Therefore, for the planning of the radiation treatment for the patient, for example, the tumor tissue and/or the organs at risk can be identified in a particularly precise manner using the magnetic resonance image data allocated to the computed tomography image data. Of course, the computed tomography image data itself can still continue to be used in a meaningful manner for the planning of the radiation treatment for the patient, for example, for delineating the bones and/or calculating the electron density map.

To support the planning of the radiation treatment, one embodiment makes provision for the computed tomography image data to be supplied for a different purpose than the magnetic resonance image data allocated to the computed tomography image data.

In a particularly advantageous manner, the procedure described makes possible the fact that both the computed tomography image data, and the magnetic resonance image data allocated to the computed tomography image data are available to support the planning of the radiation treatment for the patient. Since the magnetic resonance image data allocated to the computed tomography image data advantageously comprises image data that can complete the image data in the computed tomography image data, the magnetic resonance image data allocated to the computed tomography image data can provide support for other partial tasks when supporting the radiation treatment planning in a particularly advantageous manner than the computed tomography image data can. Thus a first set of partial tasks in the radiation treatment planning can be performed using the computed tomography image data and a second set of partial tasks in the radiation treatment planning can be performed using the magnetic resonance image data allocated to the computed tomography image data. The first set and the second set in the partial task are advantageously at least partly unconnected.

One embodiment makes provision for the computed tomography image data to support the radiation treatment planning to be made available for at least one of the following purposes:

verification of a correct positioning of the patient for radiation treatment and calculation of radiation dose during the planning of radiation treatment.

In this way, the verification of the correct positioning of the patient for radiation treatment and/or the calculation of the radiation dose during the radiation treatment planning are carried out in particular exclusively, using the computed tomography image data.

Here, the verification of the correct positioning of the patient for radiation treatment is carried out in particular using the computed tomography image data and further image data. The further image data is acquired in particular when the patient has already been positioned for radiation treatment. The further image data can include, for example, optical camera image data and/or X-ray image data and/or image data acquired via a portal imaging source in the radiation therapy device. For the verification of the correct positioning of the patient, the computed tomography image data can then advantageously be compared with the further image data.

Possible methods for the verification of the correct positioning of the patient are known to a person skilled in the art, so that these do not need to be discussed in further detail here. The computed tomography image data can be used in a particularly advantageous manner for the verification of the correct positioning of the patient for the radiation treatment, since these only have a very slight or practically no geometrical distortion and can consequently define a reliable reference geometry. The computed tomography image data can therefore be more positionally accurate than magnetic resonance image data.

For the calculation of the X-ray dose during the planning of radiation treatment, an electron density map derived from the computed tomography image data is typically used. Since the computed tomography image data in particular directly reflects a spatially resolved distribution of the electron density in the patient, the calculation of the electron density map from the computed tomography image data can then ensue in a particularly simple manner, in particular using a method known to a person skilled in the art. The electron density map calculated from the computed tomography image data can then be used, as is common practice for a person skilled in the art, for the calculation of the radiation dose in the target volume or in the patient's organs at risk, using set radiation treatment parameters.

To support the planning of the radiation treatment, one embodiment makes provision for the magnetic resonance image data allocated to the computed tomography image data to be provided for at least one of the following purposes:

a contouring of an organ structure of the patient for the radiation treatment planning and an automatic segmentation of an organ structure of the patient for the planning of radiation treatment.

In this way, the contouring of the organ structure of the patient for the radiation treatment planning and/or the automatic segmentation of the patient's organ structure for the radiation treatment planning is carried out, in particular exclusively, using the magnetic resonance image data allocated to the computed tomography image data. It is also conceivable that both the computed tomography image data and the magnetic resonance image data allocated to the computed tomography image data are used for the contouring and/or segmentation of the organ structure. Precisely for the contouring, a merged display of the computed tomography image data and of the magnetic resonance image data allocated to the computed tomography image data can be advantageous, for example.

The organ structure can be, for example, a target organ that is to be irradiated during the radiation treatment or a tumor tissue located in the target volume. Alternatively or additionally, the organ structure can be an at risk organ, which is to be spared during radiation treatment. The contouring and/or automatic segmentation of the organ structure is consequently typically fundamental to the planning of the radiation treatment.

In the contouring and/or automatic segmentation of the organ structure, the magnetic resonance image data allocated to the computed tomography image data can provide valuable additional data compared with the computed tomography image data. As already mentioned, here it is in particular the well-defined soft tissue contrast of the magnetic resonance image data allocated to the computed tomography image data that plays a major part. Since the computed tomography image data and the magnetic resonance image data allocated to the computed tomography image data have in particular been aligned three-dimensionally, the contours or the segmentation can be transposed in a particularly simple manner from the magnetic resonance image data allocated to the computed tomography image data onto the computed tomography image data for the further planning for radiation treatment, for example, for the calculation of the dose, using the electron density map calculated from the computed tomography image data.

One embodiment makes provision for the allocation of the magnetic resonance image data to the computed tomography image data to be achieved using an atlas-based method, the method comprising:

provisioning an atlas, which includes the magnetic resonance image data together with corresponding atlas-based computed tomography image data for the at least one examination subject that differs from the patient;

allocating the atlas-based computed tomography image data to the computed tomography image data; and allocating the magnetic resonance image data to the computed tomography image data using information, which is derived from the allocation of the atlas-based computed tomography image data to the computed tomography image data.

The atlas is in particular stored in a database or represents at least one part of a database. For the allocation of the magnetic resonance image data to the computed tomography image data, the atlas is then loaded in particular from the database.

The atlas-based computed tomography image data has been acquired in particular—like the magnetic resonance image data—exclusively from the at least one examination subject that differs from the patient via a computed tomography device. This means that, in particular for the acquisition of the atlas-based computed tomography image data, the patient does not have to be examined via the computed tomography device. Regarding the acquisition of the atlas-based computed tomography image data from a plurality of examination subjects that differ from the patient, reference is made to the relevant paragraph in the description of the acquisition of the magnetic resonance image data from a plurality of examination subjects that differ from the patient.

Advantageously, the atlas-based computed tomography image data and the magnetic resonance image data are acquired from the same at least one examination subject that differs from the patient. However, different examination subjects that differ from the patient can be incorporated in the acquisition of the magnetic resonance image data and the atlas-based computed tomography image data.

In the atlas, the magnetic resonance image data in particular is stored in three-dimensional alignment with the atlas-based computed tomography image data. This may mean that the magnetic resonance image data in the atlas is stored as registered with the atlas-based computed tomography image data. In particular, in the atlas at least one pair of magnetic resonance image data and corresponding atlas-based computed tomography image data that have been registered together can be stored. The magnetic resonance image data and corresponding atlas-based computed tomography image data can show an identical anatomical region, for example, a region of the head, a region of the thorax or a region of the pelvis.

To create the atlas, the magnetic resonance image data and the atlas-based computed tomography image data are advantageously acquired within as short as possible a time interval, most advantageously in a directly chronologically consecutive manner, from the examination subject that differs from the patient. In this way, there can be a particularly good anatomical match between the magnetic resonance image data and the atlas-based computed tomography image data. If the magnetic resonance image data and the atlas-based computed tomography image data are acquired from a plurality of examination subjects that differ from the patient, then advantageously, the same acquisition parameters, for example a similar CT spectrum or a similar magnetic resonance sequence, are used for the acquisition of the magnetic resonance image data and the atlas-based computed tomography image data from the plurality of the examination subjects that differ from the patient.

The atlas-based computed tomography image data can be allocated in a particularly simple manner to the patient's computed tomography image data since sets of both image data belong to the same modality. The allocation of the atlas-based computed tomography image data to the patient's computed tomography image data includes in particular a three-dimensional allocation such that the atlas-based computed tomography image data is brought into three-dimensional alignment with the patient's computed tomography image data. The allocation of the atlas-based computed tomography image data to the acquired computed tomography image data can ensue by various methods, two of which are described by way of example in the following embodiments.

The allocation of the atlas-based computed tomography image data to the computed tomography image data for the patient can offer an advantageous basis for the allocation of the magnetic resonance image data to the patient's computed tomography image data. Therefore, from the allocation of the atlas-based computed tomography image data to the computed tomography image data, allocation parameters can be acquired, for example, registration parameters such as a deformation field defined during registration. These allocation parameters can then be incorporated as input parameters in the allocation algorithm, which allocates the magnetic resonance image data to the patient's computed tomography image data.

The direct allocation of the magnetic resonance image data from the atlas to the patient's computed tomography image data, for example, using a registration, can on the other hand be difficult since both image data sets belong to different modalities. The proposed atlas-based method, which includes the use of a two-part atlas containing magnetic resonance image data and atlas-based computed tomography image data that correspond with each other, therefore offers advantageous improvements for the allocation of the magnetic resonance image data to the patient's computed tomography image data.

One embodiment makes provision for the allocation of the atlas-based computed tomography image data to the computed tomography image data to include a registration of the atlas-based computed tomography image data to the computed tomography image data, wherein the allocation of the magnetic resonance image data to the computed tomography image data ensues using a deformation field determined during the preceding registration.

The registration of the atlas-based computed tomography image data onto the computed tomography image data can ensue with a rigid, conscious, or advantageously with a non-rigid registration method. One result of the registration is then in particular the deformation field, which describes the three-dimensional deformation of the atlas-based computed tomography image data, which is necessary in order to depict the atlas-based computed tomography image data on the patient's computed tomography image data. This deformation field can then in particular be used advantageously for a deformation of the magnetic resonance image data in order to allocate these three-dimensionally to the patient's computed tomography image data. Technical details relating to atlas-based registration methods for creating an electron density map for the exclusively magnetic resonance-based radiation treatment planning are known from the document by Dowling et al. that was cited in the aforementioned, the entire contents of which are hereby incorporated herein by reference.

One embodiment makes provision for the allocation of the atlas-based computed tomography image data to the computed tomography image data to ensue using a patch-based method, wherein the allocation of the magnetic resonance image data to the computed tomography image data ensues using information obtained with the patch-based method.

For the patch-based method, the atlas-based computed tomography image data is advantageously split into a plurality of components, so-called "patches". A local similarity of the components from the atlas-based computed tomography image data to three-dimensional regions in the patient's computed tomography image data can then be determined. Based on the specific local similarity, weighting factors that can be used for a corresponding adjustment of the magnetic resonance image data to the patient's computed tomography image data can be calculated. Technical details regarding patch-based methods for creating an attenuation map based on magnetic resonance image data are known from the previously cited document by Torrado-Carvajal et al., the entire contents of which are hereby incorporated herein by reference, wherein the method described in this document can also be applied to the calculation of the electron density instead of to PET/MR attenuation correction.

One embodiment makes provision for the atlas-based computed tomography image data to be designed as dual-energy atlas-based computed tomography image data, wherein single-energy atlas-based computed tomography image data suitable for the atlas-based method is derived from the dual-energy atlas-based computed tomography image data.

Dual-energy computed tomography image data is known to a person skilled in the art so that this shall not be discussed in further detail here. The dual-energy atlas-based computed tomography image data can advantageously represent an additional source for the extraction of tissue data. To meet the respective requirement, an appropriate energy level can then be determined for the atlas-based method, at which level the single-energy atlas-based computed tomography image data is determined from the dual-energy atlas-based computed tomography image data. In this way, an appropriate allocation of the atlas-based computed tomography image data to the computed tomography image data can ensue in the atlas-based method.

One embodiment makes provision for the computed tomography image data together with the magnetic resonance image data allocated to the computed tomography image data to be provided to support the radiation treatment planning of a complete organ structure of the patient.

This procedure is based on the consideration that the magnetic resonance image data allocated to the computed tomography image data can deliver valuable additional data in the planning of radiation treatment, specifically in cases involving radiation treatment of the complete organ structure. Thus, for example, the magnetic resonance image data allocated to the computed tomography image data can supply particularly valuable additional data that can be used in the radiation treatment planning for the patient's entire prostate, entire bladder, entire rectum, or entire lung. Specifically for a more accurate contouring or segmentation of the entire prostate, the proposed procedure can be used in a particularly advantageous manner. Use of the proposed procedure in the radiation treatment planning of parts of organs, such as of part of the patient's brain or of a focused partial radiation treatment of the prostate is likewise conceivable in exceptional cases.

A further method according to at least one embodiment of the invention to support radiation treatment planning for the patient includes the following:

acquiring computed tomography image data from the patient, which has been acquired from the patient using a computed tomography device;

providing an artificial neural network that has been trained to segment an organ structure based on corresponding training magnetic resonance image data and training computed tomography image data;

segmenting the organ structure in the computed tomography image data applying the trained artificial neural network to an image content of the computed tomography image data; and providing the computed tomography image data together with the segmented organ structure to support the radiation treatment planning for the patient.

With regard to the acquisition of the computed tomography image data, reference is made to the description in one of the previous paragraphs.

The artificial neural network for the segmentation of the organ structure is uploaded in particular from a database. Here, in particular, an already trained artificial neural network is provided. An artificial neural network (ANN, but KNN in German) is in particular a network reconstructed in a computer program from artificial neurons, the artificial neural network being typically based on an interconnection of a plurality of artificial neurons. The artificial neurons are typically arranged on various layers. The artificial neural network includes an input layer and an output layer, the neuron output of which alone becomes visible as the output of the artificial neural network. Layers located between the input layer and the output layer are typically referred to as hidden layers. Typically, an architecture and/or topology of an artificial neural network is first initiated and then trained in a training phase for a specific task or for a plurality of tasks. The training of the artificial neural network typically includes a change in a weight of a connection between two artificial neurons in the artificial neural network. The training of the artificial neural network can also include development of new connections between artificial neurons, deletion of existing connections between artificial neurons, adjustment of threshold values for artificial neurons and/or addition or deletion of artificial neurons. Two different trained artificial neural networks can therefore perform different tasks although they have the same architecture and/or topology, for example.

It is now proposed that an artificial neural network trained in this way be selected to segment the organ structure, such that it allows a segmentation of the organ structure. The trained artificial neural network can be trained for a specific training task; for example, it can be suitable only for the segmentation of the organ structure in the computed tomography image data. It is conceivable that, in practice, various artificial neural networks are set up adjacent to one another and carry out segmentations of different organ structures.

In the present method, in particular, an already trained artificial neural network is provided for the segmentation of the organ structure in the computed tomography image data. The training of the artificial neural network can be carried out using the training magnetic resonance image data and the training computed tomography image data. The training magnetic resonance image data and training computed tomography image data can be configured in a similar way to the magnetic resonance image data and atlas-based computed tomography image data used in the other method according to the invention, such that reference is made here to the relevant preceding paragraphs in the description.

The segmentation of the organ structure in the computed tomography image data ensues in particular through the trained artificial neural network being applied exclusively to the image content of the computed tomography image data. Advantageously, no further image data from the patient has to be acquired for the segmentation of the organ structure. The image content of the computed tomography image data can in this way be incorporated as input data in the trained artificial neural network. The artificial neural network can then characterize as an output, in particular as the output of the artificial neurons in the output layer, those voxels in the computed tomography image data that represent a part of the organ structure that is to be segmented. In this way, the trained artificial neural network can segment the organ structure in the computed tomography image data in a particularly advantageous manner, exclusively on the basis of the image content of the computed tomography image data.

Underlying this procedure is the consideration that the artificial neural network can exclusively segment the organ structure on the basis of the image content of the computed tomography image data since it has collected experience with the segmentation of the organ structure in image data from various modalities. The artificial neural network has therefore been trained on the basis of corresponding training magnetic resonance image data and training computed tomography image data. Advantageously, additional data from a magnetic resonance tomography has also been incorporated in the training of the artificial neural network. Appropriate additional data has already been described at length in one of the previous paragraphs. The training has advantageously allowed the artificial neural network to create connections between the training magnetic resonance image data and the training computed tomography image data. In a particularly advantageous manner, these stored connections can then allow the artificial neural network to carry out the segmentation of the organ structure exclusively on the basis of the computed tomography image data.

The computed tomography image data can then be appropriately provided together with the segmented organ structure to support the radiation treatment planning for the patient. Therefore, for example, as described in greater detail in one of the previous paragraphs, a display and/or storage and/or a transmission for further processing of the computed tomography image data together with the segmented organ structure are conceivable to support the radiation treatment planning for the patient.

This method can be used in a particularly advantageous manner for the segmentation of an organ structure, which is difficult to segment using the patient's computed tomography image data alone, since for example, the organ structure in the computed tomography image data is difficult to distinguish from its surroundings. The segmentation of the organ structure can advantageously be facilitated by this procedure, without an additional acquisition of magnetic resonance image data from the patient via a magnetic resonance unit being necessary. In a particularly advantageous manner, this method is conceivable for the segmentation of the prostate to support the planning of the radiation treatment of the prostate. Organs at risk can also be segmented by way of this procedure to support the planning of the radiation treatment.

The computation unit, according to at least one embodiment of the invention, includes at least one computation module, the computation unit being designed to perform a method according to at least one embodiment of the invention.

Therefore, the computation unit in particular is designed to carry out computer-readable instructions in order to perform the method according to at least one embodiment of the invention. In particular, the computation unit includes a memory unit, computer-readable memory data being stored in the memory unit, the computation unit being designed to load the computer-readable data from the memory unit and to run the computer-readable data in order to carry out a method according to at least one embodiment of the invention.

In this way, the computation unit is designed to perform a method for supporting radiation treatment planning for a patient. For this, the computation unit can include an image data acquisition unit, which is designed for acquiring computed tomography image data from the patient, which has been acquired from the patient via a computed tomography device. To this end, the computation unit can further comprise an allocation unit, which is designed to allocate magnetic resonance image data to the computed tomography image data using the computed tomography image data, the magnetic resonance image data having been acquired via a magnetic resonance unit from the at least one examination subject that differs from the patient. Finally, the computation unit can comprise a supply unit, which is used to supply the computed tomography image data together with the magnetic resonance image data allocated to the computed tomography image data to support the radiation treatment planning for the patient.

If the computation unit is designed to carry out the further method according to at least one embodiment of the invention, in particular the computation unit will likewise comprise the image data acquisition unit. However, the supply unit is then designed in particular to supply the computed tomography image data together with the segmented organ structure to support the radiation treatment planning for the patient. Furthermore, this computation unit can then include a further supply unit to supply an artificial neural network that has been trained to segment an organ structure based on corresponding training magnetic resonance image data and training computed tomography image data. The computation unit can then also include a segmentation unit to segment the organ structure in the patient's computed tomography image data, applying the trained artificial neural network to an image content of the acquired computed tomography image data.

The components of the computation unit can mainly be designed in the form of software components. Basically, however, these components can then also be implemented partly, in particular if particularly fast calculations are involved, in the form of software-supported hardware components, for example, FPGAs or such like. Likewise, if for example, it is only an acquisition of data from other software components that is involved, the required interfaces can be designed as software interfaces. However, they can also be designed as interfaces in hardware form that are controlled by appropriate software. It is also conceivable, of course, for a plurality of the components to be implemented in groups in the form of an individual software component or of a software-supported hardware component.

The computer program product according to at least one embodiment of the invention can be loaded directly into a memory of a programmable computation unit and comprises program-coding segments in order to perform a method according to at least one embodiment of the invention when the computer program product is run in the computation unit. The computer program product can be a computer program or include a computer program. As a result thereof, the method according to at least one embodiment of the invention can be carried out quickly, in an identically repeatable manner, and robustly.

The computer program product is configured such that it can carry out the process steps according to non-transitory the invention via the computation unit. The computation unit must in each case have the prerequisites such as, for example, a corresponding main memory, an appropriate graphics card or a corresponding logic unit, such that the respective process steps can be carried out efficiently.

The computer program product of at least one embodiment is stored on a computer-readable medium, for example, or on a network or server from which it can be loaded into the processor of a local computation unit that can be directly connected thereto or designed as a component thereof. Furthermore, control data relating to the computer program product can be stored on an electronically readable data carrier. The control data on the electronically readable data carrier can be designed such that it carries out a method according to the invention when the data carrier is used in a computation unit. The computer program product can therefore also be the electronically readable data carrier. Examples of electronically readable data carriers are a DVD, a magnetic tape, a hard disk, or a USB stick, on which electronically readable control information, in particular software (see above), is stored. When this control information (software) is read by the data carrier and stored in a control device and/or computation unit, all the inventive embodiments of the method described in the aforementioned can be carried out. The invention can therefore also take as its point of departure the computer-readable medium and/or the electronically readable data carrier.

The advantages of the computer program product according to at least one embodiment of the invention and of the computation unit according to at least one embodiment of the invention essentially correspond to the advantages of the method according to at least one embodiment of the invention or of the further method according to at least one embodiment of the invention, which have been set out in detail in the aforementioned. Features, advantages or alternative embodiments referred to here shall likewise apply equally well to the other claimed subject matter and vice versa.

In other words, the substantive claims can also be further developed with the features that are described or claimed with reference to a method. The respective functional features of the method are developed in this case by respective substantive modules, in particular, by hardware modules.

FIG. 1 shows a computation unit 100 according to an embodiment of the invention for carrying out a method for supporting radiation treatment planning for a patient.

The computation unit 100 that is shown includes a plurality of computation modules 101, 102, 103, by which it is designed to carry out the method according to an embodiment of the invention. The computation unit 100 therefore includes an acquisition unit 101 for acquiring computed tomography image data from the patient. Furthermore, the computation unit 100 includes a supply unit 103 to supply the computed tomography image data together with additional data. The additional data can be the magnetic resonance image data allocated to the computed tomography image data or a segmented organ structure. The supply unit 103 can advantageously be in a data exchange with a further processing unit and/or a display unit, in order to advantageously be able to supply the computed tomography image data for the radiation treatment planning for the patient with the additional data.

The computation unit 100 includes a further computation module 102, which can carry out additional computation steps. Thus the further computation module 102 can allocate magnetic resonance image data to the computed tomography image data or segment an organ structure using a trained artificial neural network. For this purpose, the further computation module 102 is in a data exchange with a database 104, on which the magnetic resonance image data is stored, in particular in an atlas together with atlas-based computed tomography image data, or the trained artificial neural network.

The computation unit 100 that is shown can consequently be designed to carry out both of the methods according to an embodiment of the invention that have been described. The computation unit 100 can alternatively also be used only to carry out the method according to an embodiment of the invention that makes provision for the allocation of the magnetic resonance image data to the computed tomography image data. Alternatively, the computation unit 100 can also be designed only to carry out the method according to an embodiment of the invention that provides segmentation of the organ structure using the trained artificial neural network.

FIG. 2 shows a first embodiment of a method for supporting radiation treatment planning for a patient.

In a first process step 40, acquisition of computed tomography image data relating to the patient ensues via the acquisition unit 101 of the computation unit 100, the computed tomography image data having been acquired from the patient via a computed tomography device.

In a further process step 41, allocation of magnetic resonance image data to the computed tomography image data ensues using the computed tomography image data via the further computation module 102 of the computation unit 100, the magnetic resonance image data of at least one examination subject that differs from the patient having been acquired using a magnetic resonance unit.

In a further process step 42, provision of the computed tomography image data together with the magnetic resonance image data allocated to the computed tomography image data ensues using the supply unit 103 of the computation unit 100 to support the radiation treatment planning for the patient.

FIG. 3 shows a second embodiment of a method for supporting radiation treatment planning for a patient.

The description that follows is essentially restricted to the differences from the embodiment in FIG. 2, reference being made for process steps that remain the same to the description of the embodiment in FIG. 2. Process steps that essentially remain the same are basically denoted by the same reference signs.

The second embodiment of the method according to an embodiment of the invention shown in FIG. 3 essentially includes process steps 40, 41, 42 in the first embodiment of the method according to an embodiment of the invention as shown in FIG. 2. In addition, the second embodiment of the method according to the invention shown in FIG. 3 includes additional process steps and/or sub-steps. An alternative process sequence to that in FIG. 3, comprising only some of the additional process steps and/or sub-steps shown in FIG. 3, is also conceivable. An alternative process sequence to that in FIG. 3 can also of course comprise additional process steps and/or sub-steps to those shown in FIG. 3.

The computed tomography image data CT acquired in the first process step 40 is provided together with the magnetic resonance image data MR-T allocated to the computed tomography image data CT in the further process step 40 to support the radiation treatment planning for the patient. Here, the computed tomography image data CT is provided for a different purpose than the magnetic resonance image data MR-T allocated to the computed tomography image data CT. In a particularly advantageous manner, the computed tomography image data CT can then be provided together with the magnetic resonance image data MR-T allocated to the computed tomography image data CT, to support the radiation treatment planning of an entire organ structure of the patient.

In this way, the computed tomography image data CT is provided to support the radiation treatment planning for at least one first purpose P1. This first purpose P1 can include: verification of a correct positioning of the patient for radiation treatment and/or calculation of an X-ray dose during the radiation treatment planning.

To support the radiation treatment planning, the magnetic resonance image data MR-T allocated to the computed tomography image data CT is provided for a second purpose P2, which differs in particular from the first purpose P1 at least in part. This second purpose P2 can include: contouring of an organ structure of the patient for the radiation treatment planning and/or automatic segmentation of an organ structure of the patient for the radiation treatment planning.

According to FIG. 3, the allocation of the magnetic resonance image data MR-A to the computed tomography image data CT ensues in a further process step 41 using an atlas-based method. To this end, in a first partial step 41-1 of the further process step 41, an atlas is provided which includes the magnetic resonance image data MR-A together with corresponding atlas-based computed tomography image data CT-A from the at least one examination subject that differs from the patient.

Furthermore, in a second partial step 41-2 of the further process step 41, allocation of the atlas-based computed tomography image data CT-A to the computed tomography image data CT ensues. Subsequently in a third partial step 41-3 of the further process step 41, allocation of the magnetic resonance image data MR-A to the computed tomography image data CT ensues using information derived from the allocation of the atlas-based computed tomography image data CT-A to the computed tomography image data CT. The result of the allocation is then the magnetic resonance image data MR-T allocated to the computed tomography image data CT.

Here, the allocation of the atlas-based computed tomography image data CT-A to the computed tomography image data CT can include a registration of the atlas-based computed tomography image data CT-A on the computed tomography image data CT, the allocation of the magnetic resonance image data MR-A to the computed tomography image data CT ensuing using a deformation field that has been determined in a preceding registration. Alternatively, the allocation of the atlas-based computed tomography image data CT-A to the computed tomography image data CT can ensue with a patch-based method, wherein the allocation of the magnetic resonance image data MR-A to the computed tomography image data CT ensues using data acquired with the patch-based method. It is also conceivable for the atlas-based computed tomography image data CT-A to be configured as dual-energy atlas-based computed tomography image data, wherein single-energy atlas-based computed tomography image data suitable for the atlas-based method is derived from the dual-energy atlas-based computed tomography image data.

Figure 4:
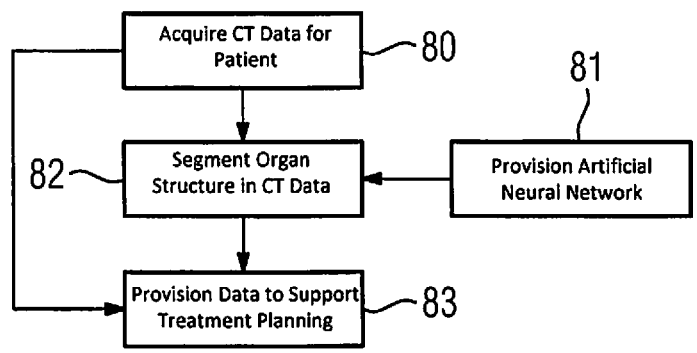

FIG. 4 shows an embodiment of a further method for supporting radiation treatment planning for a patient, which uses an artificial neural network.

In a first process step 80, acquisition of computed tomography image data for the patient ensues using the acquisition unit 101 of the computation unit 100, wherein the computed tomography image data has been acquired from the patient using a computed tomography device.

In a further process step 81, provision of an artificial neural network ensues using the further computation module 102 of the computation unit 100, which module accesses the database 104. The artificial neural network has been trained in segmenting an organ structure based on corresponding training magnetic resonance image data and training computed tomography image data.

In a further process step 82, segmentation of the organ structure ensues in the computed tomography image data via the further computation module 102 of the computation unit 100 applying the trained artificial neural network to an image content of the computed tomography image data.

In a further process step 83, provision of the computed tomography image data together with the segmented organ structure ensues via the supply unit 103 of the computation unit 100 to support the radiation treatment planning for the patient.

The process steps of the method according to embodiments of the invention shown in FIGS. 2-4 are carried out by the computation unit. To this end, the computation unit includes the software and/or computer programs that are stored in a memory unit of the computation unit. The software and/or computer programs include programming segments designed to carry out the method according to embodiments of the invention when the computer program and/or the software is/are run in the computation unit using a processor unit of the computation unit.

Figure 5:
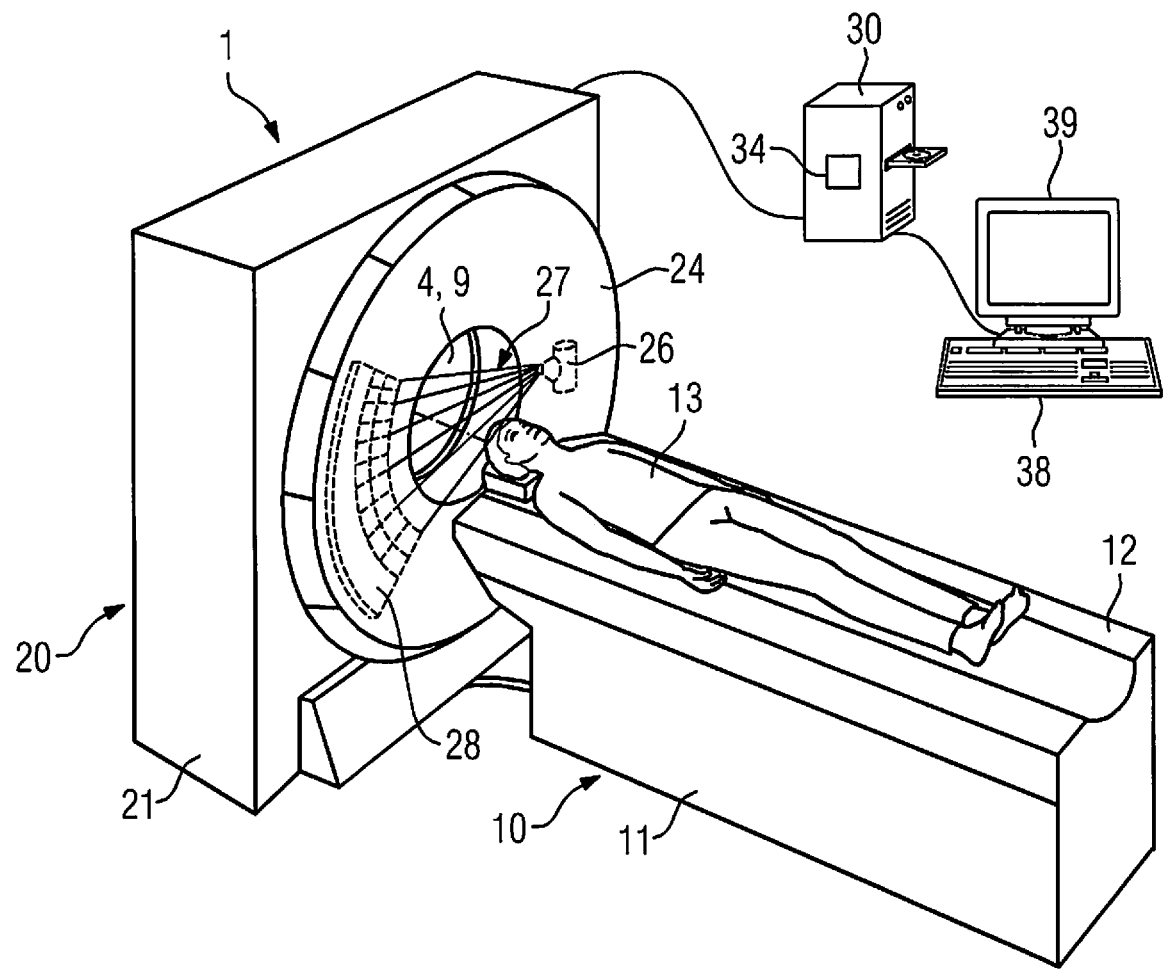

FIG. 5 shows a computed tomography device 1 for acquiring the computed tomography image data relating to the patient. The computed tomography image data acquired using the computed tomography device 1 can be used to support the radiation treatment planning for the patient. To this end, the computed tomography image data can be transmitted from the computed tomography device 1 to the computation unit 100 according to the invention, which can acquire the computed tomography image data using the acquisition unit 101 and subsequently further process it.

The computed tomography device 1 comprises a gantry 20, a tunnel-shaped aperture 9, a patient-positioning device 10 and a control device 30. The gantry 20 comprises a stationary supporting frame 21 and a rotor 24. The rotor 24 is rotatably arranged on the stationary supporting frame 21 via a rotating positioning device round an axis of rotation relative to the stationary supporting frame 21. A patient 13 can be guided into the tunnel-shaped aperture 9. In the tunnel-shaped aperture 9, an acquisition region 4 is located. In the acquisition region 4, a region of the patient 13 that is to be imaged is positionable such that electromagnetic radiation 27 from a radiation source 26 can reach the region that is to be imaged and after an interaction with the region that is to be imaged can reach a radiation detector 28. The patient-positioning device 10 comprises a positioning table 11 and a transfer plate 12 for positioning the patient 13. The transfer plate 12 is moveably arranged on the positioning table 11 relative to the positioning table 11 such that the transfer plate 12 can be guided into the acquisition region 4 in a longitudinal direction of the transfer plate 12.

The computed tomography device 1 is designed to acquire projection data based on the electromagnetic radiation 27. The computed tomography device 1 includes a projection data acquisition unit comprising the radiation source 26, in particular an X-ray source, and the detector 28, an X-ray detector for example, in particular an energy-resolved X-ray detector. The radiation source 26 is arranged on the rotor 24 and is designed to emit radiation 27, in particular X-rays, with radiation quanta 27. The detector 28 is arranged on the rotor 24 and is designed to detect the radiation quanta 27. The radiation quanta 27 can reach from the radiation source 26 to the region of the patient 13 that is to be imaged and after interaction with the region that is to be imaged can impinge on the detector 28. In this way, projection data for the region that is to be imaged can be acquired using the acquisition unit.

A control apparatus 30 is designed to receive the projection data acquired by the acquisition unit. The control apparatus 30 is designed to control the computed tomography device 1. The control apparatus 30 comprises an image reconstruction unit 34. By way of the image reconstruction unit 34, computed tomography image data can be reconstructed on the basis of the projection data.

The computed tomography device 1 comprises an input unit 38 and a display unit 39, each of which are connected to the control apparatus 30. The input unit 38 is designed to input control data, for example image reconstruction parameters and/or examination parameters. The display unit 39 is designed in particular to display the computed tomography image data.

Although the invention has been illustrated and described in greater detail with the preferred embodiments, the invention is not, however, restricted to the examples disclosed, and other variants can be derived therefrom by a person skilled in the art, without going beyond the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for planning radiation treatment for a patient, the method comprising:
   acquiring computed tomography image data for the patient via a computed tomography device;
   registering magnetic resonance image data to the computed tomography image data using the computed tomography image data, the magnetic resonance image data having been acquired from at least one examination subject via a magnetic resonance imaging unit, the at least one examination subject being different from the patient; and
   providing the computed tomography image data and the magnetic resonance image data for planning the radiation treatment for the patient.

2. The method of claim 1, wherein the computed tomography image data is for a different application than the magnetic resonance image data.

3. The method of claim 2, wherein the computed tomography image data is for at least one of
   verification of correct positioning of the patient for the radiation treatment or
   calculation of an X-ray dose during the planning of the radiation treatment.

4. The method of claim 2, wherein the magnetic resonance image data is provided for at least one of
   a contouring of an organ structure of the patient for the planning of the radiation treatment, or
   an automatic segmentation of an organ structure of the patient for the planning of the radiation treatment.

5. The method of claim 1, wherein the registering of the magnetic resonance image data to the computed tomography image data utilizes an atlas-based method, and the registering comprises:
   providing an atlas, including the magnetic resonance image data together with corresponding atlas-based computed tomography image data for the at least one examination subject;
   registering the atlas-based computed tomography image data to the computed tomography image data; and
   registering the magnetic resonance image data to the computed tomography image data using information derived from the registering of the atlas-based computed tomography image data to the computed tomography image data.

6. The method as claimed in claim 5, wherein the registering of the magnetic resonance image data to the computed tomography image data utilizes a deformation field defined in a preceding registration.

7. The method as claimed in claim 5, wherein
   the registering of the atlas-based computed tomography image data to the computed tomography image data utilizes a patch-based method, and
   the registering of the magnetic resonance image data to the computed tomography image data utilizes information obtained with the patch-based method.

8. The method of claim 5, wherein
   the atlas-based computed tomography image data is dual-energy atlas-based computed tomography image data, and
   the method further includes
      deriving single-energy atlas-based computed tomography image data for the atlas-based method from the dual-energy atlas-based computed tomography image data.

9. The method of claim 1, wherein the computed tomography image data and the magnetic resonance image data are provided to support planning of radiation treatment of a complete organ structure of the patient.

10. A method for planning radiation treatment for a patient, the method comprising:
   acquiring computed tomography image data for the patient via a computed tomography device;
   providing an artificial neural network, the artificial neural network trained to segment an organ structure based on corresponding training magnetic resonance image data and training computed tomography image data;
   segmenting the organ structure in the computed tomography image data by applying the artificial neural network to image content of the computed tomography image data; and
   planning the radiation treatment for the patient based on the computed tomography image data together with the segmented organ structure.

11. A computation device, comprising:
at least one processor configured to execute computer-readable instructions to cause the computation device to
   acquire computed tomography image data for patient via a computed tomography device,
   register magnetic resonance image data to the computed tomography image data using the computed tomography image data, the magnetic resonance image data having been acquired from at least one examination subject via a magnetic resonance imaging unit, the at least one examination subject different from the patient, and
   provide the computed tomography image data and the magnetic resonance image data for planning radiation treatment for the patient.

12. A non-transitory computer program product, directly loadable into a memory of a programmable computation unit, the non-transitory computer program product comprising program-coding segments to perform the method of claim 1 when the program-coding segments are executed on the programmable computation unit.

13. The method of claim 3, wherein the magnetic resonance image data is for at least one of
   contouring of an organ structure of the patient for the planning of the radiation treatment, or
   an automatic segmentation of an organ structure of the patient for the planning of the radiation treatment.

14. The method of claim 2, wherein the registering of the magnetic resonance image data to the computed tomography image data utilizes an atlas-based method, and the registering comprises:
   providing an at atlas including the magnetic resonance image data together with corresponding atlas-based computed tomography image data for the at least one examination subject;
   registering the atlas-based computed tomography image data to the computed tomography image data; and
   registering the magnetic resonance image data to the computed tomography image data using information derived from the registering of the atlas-based computed tomography image data to the computed tomography image data.

15. The method as claimed in claim 14, wherein
the registering of the magnetic resonance image data to the computed tomography image data utilizes a deformation field defined in a preceding registration.

16. The method as claimed in claim 14, wherein
the registering the atlas-based computed tomography image data to the computed tomography image data utilizes a patch-based method, and
the registering the magnetic resonance image data to the computed tomography image data utilizes information obtained with the patch-based method.

17. The method of claim 14, wherein
the atlas-based computed tomography image data is dual-energy atlas-based computed tomography image data, and
the method further includes
   deriving single-energy atlas-based computed tomography image data for the atlas-based method from the dual-energy atlas-based computed tomography image data.

18. The method of claim 6, wherein
the atlas-based computed tomography image data is dual-energy atlas-based computed tomography image data, and
the method further includes
   deriving single-energy atlas-based computed tomography image data for the atlas-based method from the dual-energy atlas-based computed tomography image data.

19. The method of claim 7, wherein
the atlas-based computed tomography image data is dual-energy atlas-based computed tomography image data, and
the method further includes
   deriving single-energy atlas-based computed tomography image data for the atlas-based method from the dual-energy atlas-based computed tomography image data.

20. A non-transitory computer program product, directly loadable into a memory of a programmable computation unit, the non-transitory computer program product comprising program-coding segments to perform the method of claim 10 when the program-coding segments are executed on the programmable computation unit.

21. A non-transitory computer readable medium including program code for carrying out the method of claim 1 when the program code is executed on a computer.

22. A non-transitory computer readable medium including program code for carrying out the method of claim 10 when the program code is executed on a computer.

23. The method of claim 1, further comprising:
planning the radiation treatment for the patient at least partly based on the computed tomography image data and the magnetic resonance image data and without acquiring magnetic resonance image data for the patient.

24. The method of claim 23, further comprising:
performing the radiation treatment on the patient.

25. The computation device of claim 11, wherein the at least one processor is further configured to execute computer-readable instructions to cause the computation device to plan the radiation treatment for the patient at least partly based on the computed tomography image data and the magnetic resonance image data, and without acquiring magnetic resonance image data for the patient.

* * * * *